United States Patent
Sheskey et al.

(10) Patent No.: US 7,011,702 B2
(45) Date of Patent: Mar. 14, 2006

(54) AQUEOUS AIR FOAM

(75) Inventors: Paul J. Sheskey, Midland, MI (US); Colin M. Keary, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/484,996

(22) PCT Filed: Aug. 23, 2002

(86) PCT No.: PCT/US02/26786

§ 371 (c)(1), (2), (4) Date: May 27, 2004

(87) PCT Pub. No.: WO03/020207

PCT Pub. Date: Mar. 13, 2003

(65) Prior Publication Data

US 2004/0209966 A1 Oct. 21, 2004

Related U.S. Application Data

(60) Provisional application No. 60/317,403, filed on Sep. 4, 2001.

(51) Int. Cl.
C08L 1/28 (2006.01)
C09D 101/28 (2006.01)
B05D 1/34 (2006.01)
(52) U.S. Cl. ............ 106/122; 106/172.1; 427/2.14; 427/212; 427/213.3; 427/430.1

(58) Field of Classification Search ............ 106/122, 106/172.1; 427/2.14, 212, 213.3, 430.1
See application file for complete search history.

(56) References Cited

U.S. PATENT DOCUMENTS

| | | | | |
|---|---|---|---|---|
| 3,334,052 A | * | 8/1967 | Kurz et al. ............ | 516/105 |
| 3,963,507 A | * | 6/1976 | Kuramoto et al. ...... | 523/83 |
| 4,511,497 A | | 4/1985 | Ehrlich ................. | 252/542 |
| 4,683,004 A | | 7/1987 | Goddard ............... | 106/170 |
| 5,026,735 A | | 6/1991 | Stern ................... | 521/50 |
| 5,554,658 A | | 9/1996 | Rosenblatt ............ | 521/51 |
| 6,258,374 B1 | | 7/2001 | Friess et al. .......... | 424/436 |
| 6,780,230 B1 | * | 8/2004 | Hilton et al. .......... | 106/122 |

FOREIGN PATENT DOCUMENTS

| | | |
|---|---|---|
| EP | 0 362 655 | 4/1990 |
| EP | 1 120 109 | 8/2001 |
| WO | WO 91/13138 | 9/1991 |

OTHER PUBLICATIONS

J. Appl. Chem. 1, 425-429 (1951), "A mechanical foam generator for use in labortories". J.F. Fry & R.J. French.

* cited by examiner

*Primary Examiner*—David Brunsman

(57) ABSTRACT

An aqueous air foam comprising a non-crosslinked cellulose ether selected from C1–C3-alkyl celluloses, C1–C3-alkyl-hydroxy-C1–3-alkyl celluloses, hydroxy-C1–3-alkyl celluloses, or mixed hydroxy-C1–C3-alkyl celluloses, the foam having quality FQ of from 60 to 97 percent and the foam quality being defined as FQ (%)=(air volume÷(air volume+fluid volume)×100).

19 Claims, 2 Drawing Sheets

AQUEOUS AIR FOAM

This application is a 371 of PCT/US02/26786, filed Aug. 23, 2002 which claims the benefit of Provisional Application No. 60/317,403, filed Sep. 4, 2001.

The present invention relates to aqueous air foam and to the use of such air foam.

BACKGROUND OF THE INVENTION

Aqueous foams are generally known.

U.S. Pat. No. 4,683,004 discloses foamable compositions and their use as hair styling mousses and foaming hand lotions and cleansers. The foamable composition comprises water and a foam stabilizer. The foam stabilizer is a non-ionic cellulose ether which is substituted with methyl, hydroxyethyl or hydroxypropyl groups and which further is substituted with a long chain alkyl radical having 10 to 24 carbon atoms. The foamable composition comprises a hydrocarbon propellant.

European patent application EP-A-0 362 655 discloses foamable pharmaceutical compositions which comprise water, a gel forming agent, an effective amount of a drug and a propellant. The gel forming agent preferably is a water-soluble cellulose derivative, such as methylcellulose, or gelatin. The propellant is preferably carbon dioxide and nitrous oxide.

For easy availability of the gas and for environmental reasons, it is desirable to provide aqueous air foams which are useful for various applications, that means foams which are made by physically mixing air into a fluid.

U.S. Pat. No. 5,026,735 relates to the treatment of hazardous material or other substrate with aqueous air foam. The foam is produced from a water-based composition which comprises (a) a water-soluble polyhydroxy polymer, such as guar gum or poly(vinyl alcohol), (b) a polyvalent ionic complexing agent, such as borax, (c) a foaming agent, such as various surfactants, (d) a pH modifier, and (e) water as the main component.

One object of the present invention is to provide new aqueous air foam which is suitable for various uses, such as powder granulation or coating solid particles like tablets.

SUMMARY OF THE INVENTION

One aspect of the present invention is an aqueous air foam which comprises a non-crosslinked cellulose ether selected from $C_1$–$C_3$-alkyl celluloses, $C_1$–$C_3$-alkyl hydroxy-$C_{1-3}$-alkyl celluloses, hydroxy-$C_{1-3}$-alkyl celluloses or mixed hydroxy-$C_1$–$C_3$-alkyl celluloses, wherein the foam has a foam quality FQ of from 60 to 97 percent and the foam quality is defined as FQ(%)=[air volume/(air volume+fluid volume)×100].

Another aspect of the present invention is the use of the above-mentioned foam for agglomerating solid particles.

Yet another aspect of the present invention is the use of the above-mentioned foam for coating solid particles.

Yet another aspect of the present invention is a process for agglomerating solid particles wherein the above-mentioned foam is contacted with the solid particles to be agglomerated.

Yet another aspect of the present invention is a process for coating solid particles wherein the above-mentioned foam is contacted with the solid particles to be coated.

SHORT DESCRIPTION OF THE DRAWINGS

DETAILED DESCRIPTION OF THE INVENTION

Figure 1:
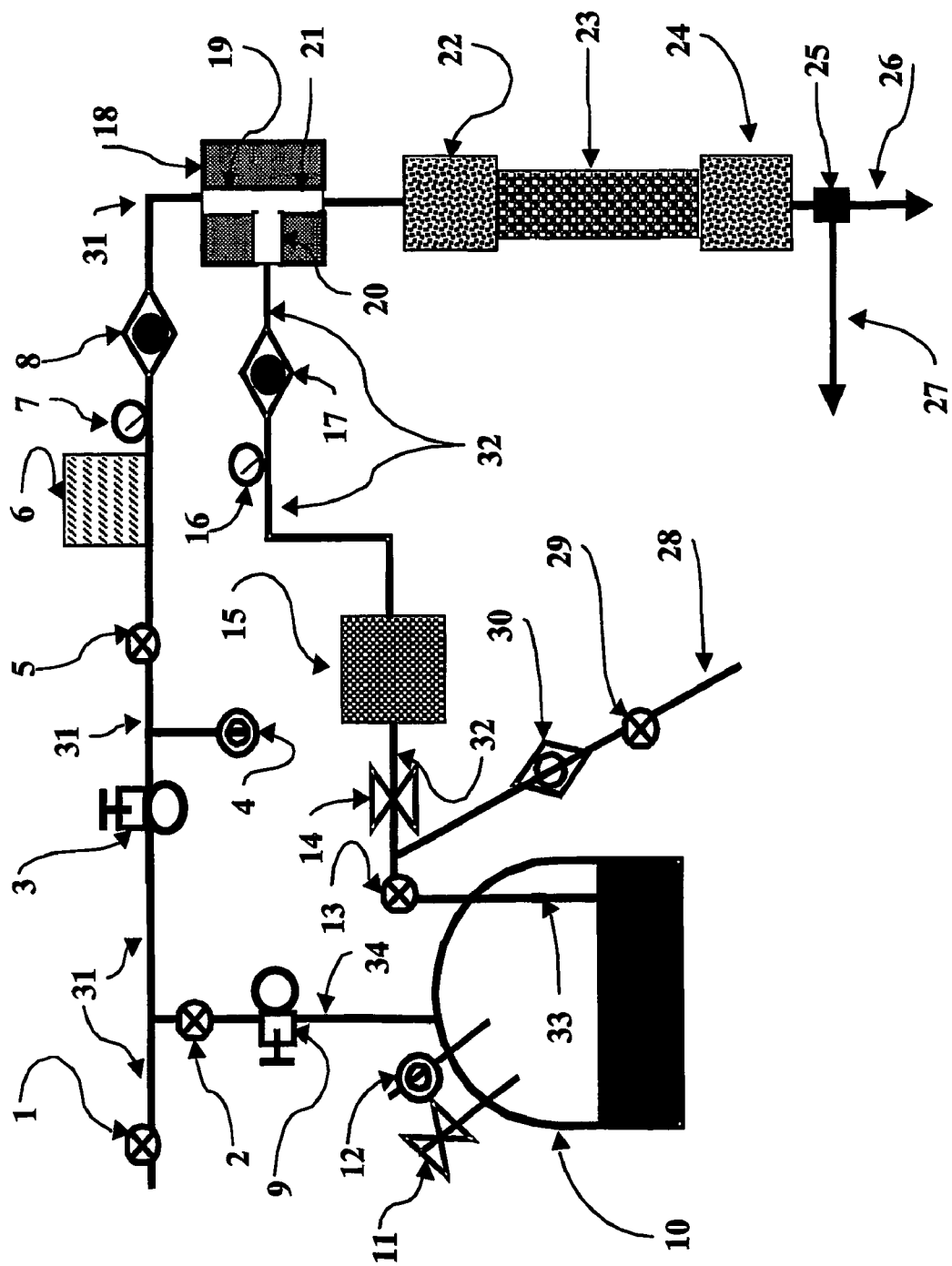
FIG. 1 illustrates a foam-generating device for producing the foam of the present invention.

The foam of the present invention is an air aqueous foam. This means that more than 50 weight percent, preferably at least 60 weight percent, more preferably at least 75 weight percent and most preferably at least 95 weight percent of the liquid comprised in the foam is water. The term "air foam" is used in its industry-accepted sense to mean a foam made by physically mixing air into a fluid, and thus the term is distinct from chemical or carbon dioxide foam or halocarbon blown foam. The foam may contain a minor amount of a gas other than air, such as carbon dioxide, or a hydrocarbon or halocarbon that is gaseous at room temperature and atmospheric pressure. However the air should amount to at least 70 percent, preferably at least 80 percent, more preferably at least 95 percent of the entire gas volume. Most preferably, the foam does not contain another gas than air.

The foam of the present invention comprises a non-crosslinked cellulose ether selected from $C_1$–$C_3$-alkyl celluloses, such as methylcelluloses; $C_1$–$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; or mixed hydroxy-$C_1$–$C_3$-alkyl celluloses, such as hydroxyethyl hydroxypropyl celluloses. Preferably, water-soluble cellulose ethers are comprised in the foam. More preferably, the foam comprises a methylcellulose or a hydroxypropyl methylcellulose. Most preferably, the foam comprises a methylcellulose with a methyl molar substitution $DS_{methoxyl}$ of from 0.5 to 3.0, preferably from 1 to 2.5, or a hydroxypropyl methylcellulose with a $DS_{methoxyl}$ of from 0.5 to 3.0, preferably from 1 to 2.5 and a $MS_{hydroxypropoxyl}$ of from 0.05 to 2.0, preferably from 0.1 to 1.5. The viscosity of the cellulose ether preferably is from 1 to 100,000 mPa·s, more preferably from 3 to 10,000 mPa·s, most preferably from 5 to 5,000 mPa·s, measured as a 2-wt. % aqueous solution at 20° C. using an Ubbelohde viscometer.

The aqueous air foam generally comprises from 0.01 to 30 percent, preferably from 0.1 to 20 percent, more preferably from 0.5 to 15 percent, and most preferably from 1 to 5 percent of the non-crosslinked cellulose ether and from 99.99 to 70 percent, preferably from 99.9 to 80 percent, more preferably from 99.5 to 85 percent, and most preferably from 99 to 95 percent of water, based on the total weight of the cellulose ether and water.

Preferably, the foam does not comprise a substantial amount of a surfactant other than the cellulose ether. This means that an aqueous fluid composition which comprises an above-mentioned cellulose ether and which is used for preparing the foam of the present invention preferably does not contain a surfactant other than the cellulose ether in a sufficient amount to cause foaming of the fluid composition upon contact with air. More preferably, the fluid composition does not comprise any amount of a surfactant other than the cellulose ether. Most preferably, the fluid composition does not comprise a known nonionic, cationic, anionic or amphoteric surfactant, as for example listed in U.S. Pat. No. 5,026,735, column 6, lines 47–68 and column 7, lines 1–22.

The foam may contain one or more additional solid or liquid components such as drugs, fillers, pigments flavors or plasticizers. If present, their total amount is generally up to 75 percent, preferably up to 50 percent, more preferably up to 25 percent, based on the total weight of the foam. A two-phase foam is composed of an aqueous phase and a gaseous phase. A three-phase foam may comprise, in addition to aqueous and gaseous phases, insoluble solids or immiscible liquids. Such three-phase foams can also contain dissolved solids in the aqueous or immiscible liquid phase or in both liquid phases. Four-phase foams may comprise, in addition to aqueous and gaseous phases, immiscible liquids and insoluble solids. In all foams, any immiscible liquid phase may be present as an oil-in-water or water-in-oil emulsion or as a simple dispersion.

For producing the foam of the present invention a fluid composition comprising water, one or more of the above-mentioned cellulose ethers and optionally one or more of the above-mentioned additives is contacted with air to produce a foam. The foam can be produced in a known manner by mechanically or physically entraining or dispersing the air in the fluid composition, for example by pumping the fluid composition to air-aspirating, foam producing equipment. One useful and simple foam generating device is shown in FIG. 1.

The produced foam comprises a discontinuous air phase, and a continuous aqueous phase, comprising the polymer and bound liquid. Generally the lamella or fluid film of the air bubbles is viscous due to the presence of the polymer. Water is retained in the lamella of the air bubbles. The drainage of the liquid from the lamellae is minimized, reduced or prevented; such foam is designated as "non-draining foam" in the art.

The foam of the present invention generally has an average bubble diameter in the range of from about 1 micrometer to about 2,000 micrometers, preferably from about 5 micrometers to about 1,000 micrometers, more preferably from about 10 micrometers to about 300 micrometers. It is to be understood that the measurements of the foam diameter generally are not very accurate in view of the dynamic properties of the foam.

The foam preferably has a measured density of up to 0.1 g/cm$^3$.

It has been found that the foam of the present invention has a surprisingly high foam quality. The foam quality FQ is given in percent at atmospheric pressure and 25° C. and is defined as follows:

$$FQ(\%) = [\text{gas volume}/(\text{gas volume} + \text{fluid volume}) \times 100].$$

The foam quality can be measured by measuring the foam volume that is produced from a given volume of fluid at atmospheric pressure and 25° C. The foams of the present invention have a foam quality of from 60 to 97 percent, preferably from 65 to 95 percent, more preferably from 75 to 95 percent. Such high foam quality is surprising for non-draining foams. The foam quality FQ as defined herein is the measured foam quality.

It has been observed that the above-mentioned measured foam quality FQ is surprisingly close to the theoretical foam quality $FQ_T$.

$$FQ_T = [V \text{ supplied gas}/(V \text{ supplied gas} + V \text{ supplied fluid}) \times 100],$$

wherein V means the volume at 25° C. and atmospheric pressure that is supplied per time unit during the foam production, for example the supplied volume per minute. It goes without saying that the same time unit has to be taken for the supplied volume of gas and the supplied volume of fluid to calculate $FQ_T$.

Surprisingly, is has been found that the theoretical foam quality $FQ_T$ is generally only up to 1.75 times as high, in many cases even only up to 1.5 times as high, and in the most preferred embodiments of the invention only up to 1.2 times as high as the measured foam quality FQ. Such a high measured foam quality is highly desirable. The low liquid content in the foam reduces the time which is necessary for drying the foam after its use, for example for drying powder which has been agglomerated with the foam or for drying particles which have been coated with the foam of the present invention.

It has surprisingly been found that foams can be produced which are useful in various applications, such as granulating solid particles like powders or coating solid particles like tablets, even when the volume of the supplied gas is very large, as compared to the volume of the supplied liquid in a foam generating device. For example, gases with a theoretical foam quality $FQ_T$ as high as 99.8 percent have shown to give excellent results in powder granulation trials. As indicated above, the aqueous air foam of the invention comprising non-crosslinked cellulose ether is a non-draining foam. Skilled artisans expect for non-draining foams the formation of a mist, this means the formation of liquid droplets in air, when the theoretical foam quality $FQ_T$ is about 96 percent or higher. In known non-draining foams with a theoretical foam quality $FQ_T$ of about 96 percent or more, the foam bubbles deform from spherical to multihedral to increase the packing efficiency of the bubbles. The foam bubbles may only deform by displacing liquid from the lamellae. The displaced liquid eventually forms liquid droplets in air.

Figure 2:
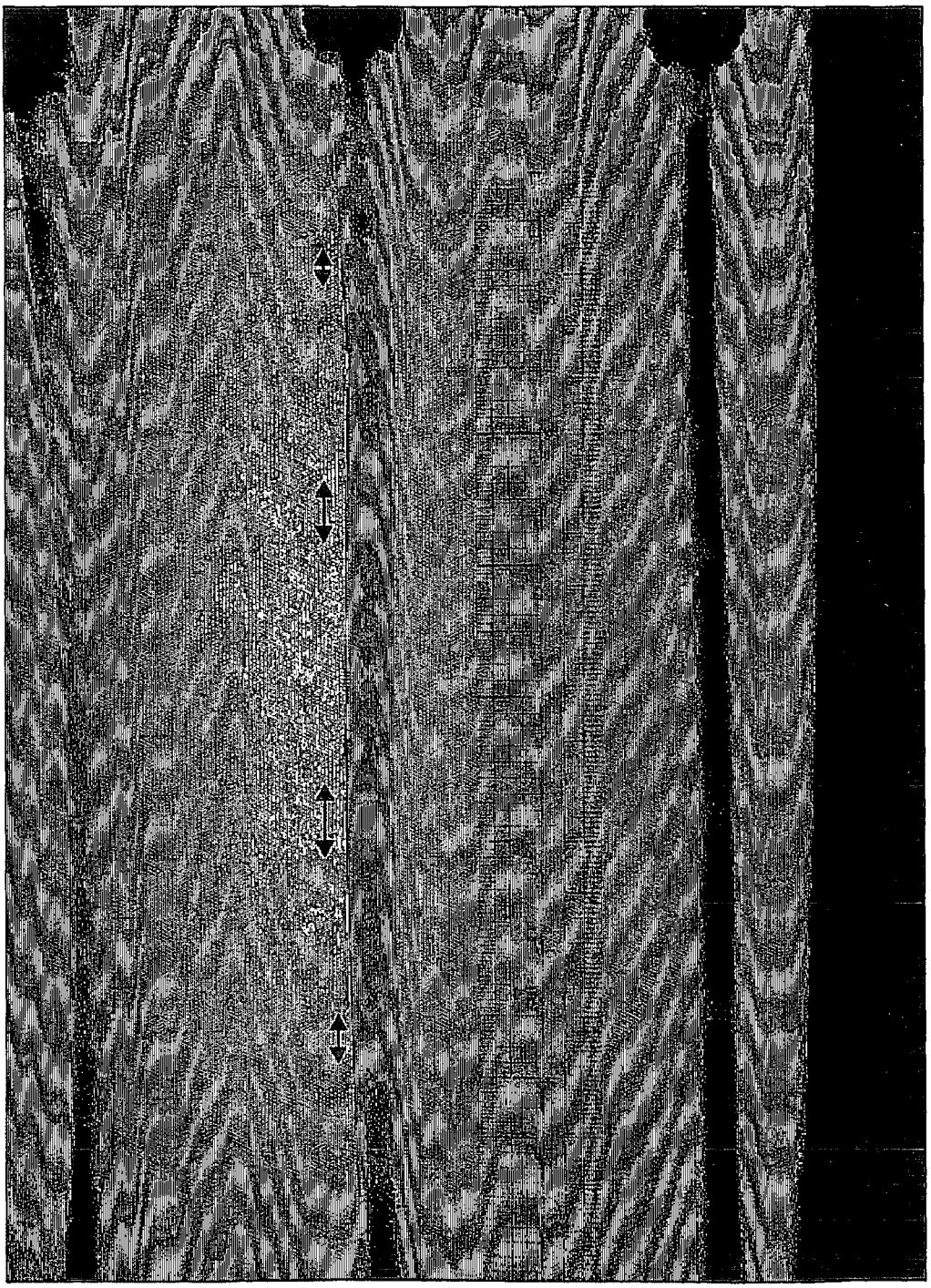
FIG. 2 represents a photograph of foam flowing through a tube of the foam-generating device illustrated in FIG. 1.

Surprisingly, it has been found that useful foams can be produced with a higher supplied and measured air/water ratio, that means a higher measured foam quality FQ, than can be expected for non-draining foams with spherical bubbles. Generally the foams of the present invention can have a theoretical foam quality $FQ_T$ of from 65 to 99.9 percent, preferably of from 75 to 99.8 percent, more preferably from 85 to 99.8 percent. Even at a theoretical foam quality $FQ_T$ of more than 96 percent, the formation of a mist has not been observed. Without wanting to be bound to the theory, it is believed that this unexpectedly high foam quality that can be achieved in the foam of the present invention is due to pockets of air which are entrapped in pockets of foam. Pockets of foam interspersed with pockets of air have been observed in foams of the present invention. FIG. 2 represents a photograph of foam of the present invention flowing through a tube of a foam-generating device. Air-foam boundaries are visible, which indicates that pockets of foam are interspersed with pockets of air.

It has been found that one way of producing foam of a higher measured foam quality FQ is the production of the foam in a foam generating device under pressure by contacting a stream of the above-described fluid composition comprising water, one or more of the above-mentioned cellulose ethers and optionally one or more of the above-mentioned additives with a stream of air and to release the produced foam to ambient pressure. The pressure of the aqueous fluid stream preferably is from 135 to 1,100 kPa, more preferably from 350 to 700 kPa, most preferably about 414 kPa. The pressure of the air stream is preferably from 13 to 70 kPa lower, more preferably from 20 to 50 kPa lower, most preferably from 25 to 40 kPa lower than the pressure of the aqueous fluid stream. When the foam is released from the foam generating device operating under pressure, the foam expels excess air to maintain its foam structure. Expelled air forms pockets of air within the foam.

The foam of the present invention is useful for agglomerating solid particles, such as a powder. The particles can be of any shape, such as spherical, elliptic, or fibrous. The solid particles generally has an average particle size of less than 2500 micrometers, preferably less than 1000 micrometers, more preferably less than 750 micrometers, most preferably less than 500 micrometers. The foam of the present invention is particularly useful for agglomerating powders. Therefore, the following description refers to powders although the agglomeration process is not limited to powders. The weight ratio between the foam and the powder generally is from 1:20 to 1:0.2, preferably from 1:10 to 1:0.5, more preferably from 1:5 to 1:1. Preferably, the foam and the powder are contacted in such ratios that the amount of the above-mentioned cellulose ether is from 0.02 to 15, more preferably from 0.1 to 10, most preferably from 0.15 to 8 percent, based on the weight of the powder. The foam can be contacted with a wide variety of powders. Any powder is useful which traditionally has been coated or agglomerated with a fluid. Preferred classes of useful powders are ingredients of pharmaceutical granules or tablets, ingredients for granules or tablets used in the food or agricultural industry, powders used in ceramic processes, or powdered detergents. It has been found that the foam lamellae generally break and reform as they pass through the powder during granulation.

Advantageously the contact of the foam with the powder is conducted in a mixing device, such as a high shear mixing device, a low shear mixing device, a fluidized bed granulator, a roller compactor or a spray dryer. The contact of the foam with powder can be carried out in various ways.

According to one way of powder agglomeration, the mixing device is set into operation after the powder and the foam have been fed to the mixing device. Preferably, the powder is fed to the mixing device, foam is placed on top of the powder and the mixing device is subsequently set into operation. This method prevents dust emission during the agglomeration step. Surprisingly, is has been found that a uniform dispersion of the foam in the powder can be achieved within a very short period after the mixing device has been set in operation, usually within less than 30 seconds, in most cases even within less than 10 seconds, even when the entire amount of foam is placed on top of the powder and the mixing device is set into operation only afterwards. This finding is in contrast to known processes wherein a corresponding liquid composition is directly dispersed in the powder without formation of foam from the fluid composition. If the liquid is added on top of the powder, large lumps are formed and a uniform dispersion of the liquid in the powder is impossible.

According to another way of powder agglomeration, powder and a foam portion are fed to a mixing device, the mixing device is set into operation to disperse the foam portion in the powder, the operation of the mixing device is stopped, an additional foam portion is fed to the mixing device, and the previous steps are repeated several times.

Alternatively, the powder is loaded into a mixing device and foam is added continuously or in portions to the mixing device while the mixing device is in operation.

According to the described process of agglomerating powders a surprisingly homogeneous dispersion of the cellulose ether and optional other foam components in the powder is achieved. Moreover, a simple device can be used for applying the foam to the powder, such as a simple tube.

Maintenance-intensive, expensive and complex atomizing devices that are commonly used for spraying fine droplets of liquids on a powder in know agglomeration processes with liquids are not necessary. The dispersion of the foam in the powder is achieved at a rate which is comparable to or even faster than the dispersion of a corresponding liquid spray in the powder. The described method of agglomerating powders is also useful for dispersing poorly water-soluble compounds, such as poorly water-soluble drugs, in the powder.

The foam of the present invention is also useful for coating solid particles, such as tablets, granules, pellets, caplets, capsules, lozenges, suppositories, pessaries or implantable dosage forms. The weight ratio between the foam and the solid particles generally is from 1:20 to 1:0.002, preferably from 1:10 to 1:0.01, more preferably from 1:5 to 1:0.1. Preferably, the foam and the solid particles are contacted in such ratios that the amount of the above-mentioned cellulose ether is from 0.01 to 20, more preferably from 0.05 to 15, most preferably from 0.075 to 10 percent, based on the weight of the solid particles. The solid particles are preferably agitated, such as tumbled, dipped through the foam or otherwise moved during the coating. The agitation of the particles can be started before, during or after the contact of the particles with the foam. However, agitation of the particles is preferably started before the foam is added to the particles and is continued during the foam addition. More preferably, foam is added to continuously agitated solid particles. The coating can be conducted in a known coating device, for example in a tumbler, perforated side-vented coating pan, Wurster column insert in a fluid-bed device, low-shear blender or a continuous coating device of any configuration. Preferably, the foam is added continuously or semi-continuously to agitated solid particles. The foam can be added to the solid particles by means of a simple tube of which the end is placed closely to or into the mass of solid particles. A surprisingly smooth coating of constant thickness on the solid particles is achieved. Usually up to 5 coats, in most cases only up to 3 coats, typically even 1 to 2 coats are sufficient to provide a glossy, smooth coating of constant thickness and good gloss.

The present invention is further illustrated by the following examples which should not be construed to limit the scope of the present invention. All parts and percentages are by weight unless otherwise indicated.

The alkyl and hydroxyalkyl substitutions of the cellulose ethers indicated in the examples below are measured and calculated according to ASTM D3876.

The apparent viscosities indicated in the examples below are measured and normalized to a 2 weight percent aqueous solution using an Ubbelohde viscometer at 20° C. The foam quality FQ is measured by filling a container of 280 ml volume with foam at 25° C. and atmospheric pressure, centrifuging the foam to collapse it and measuring the volume of the resulting liquid. The foam quality is measured according to the following formula:

$$FQ(\%) = [\text{gas volume}/(\text{gas volume} + \text{fluid volume}) \times 100].$$

EXAMPLES 1–3

In Example 1 an aqueous solution containing 1 weight percent of a hydroxypropyl methylcellulose described below is prepared.

In Example 2 an aqueous solution containing 1 weight percent of a hydroxypropyl methylcellulose described below and 0.001 weight percent of a sodium lauryl sulfate, a surfactant, is prepared.

In Example 3 an aqueous solution containing 5 weight percent of a hydroxypropyl methylcellulose described below is prepared.

The hydroxypropyl methylcellulose has a methoxyl substitution of 28–30 percent, a hydroxypropoxyl substitution of 7–12 percent and a viscosity of about 6 mPa·s. The hydroxypropyl methylcellulose is commercially available from The Dow Chemical Company under the Trademark METHOCEL E6PLV.

From the aqueous solution a foam is prepared as illustrated in FIG. 1. Air flows through a tube 31 equipped with ball valves 1, 2 and 5, with pressure regulators and gauge 3 and 9, with a pressure relief valve 4, a mass flow controller 6, a pressure gauge 7 and a check valve 8. The pressure in tube 31 is regulated to about 414 kPa. The aqueous solution is passed from a pressure vessel 10, which is equipped with a pressure relief valve 12, needle valve 11, air inlet tube 34 and a dip-pipe 33, through a tube 32. The pressure in tube 32 is regulated to about 414 kPa. Tube 32 is equipped with a ball valve 13, a needle valve 14, an oval gear flow meter 15, a pressure gauge 16 and a check valve 17 and with a water supply line 28, a ball-valve 29 and a check valve 30. The air stream and fluid stream meet in T-piece 18 comprising an air-inlet port 19, a fluid inlet port 20 and a foam outlet port 21. The air stream is dispersed in the water stream by in-line filters 22 and 24 and additionally in packed tube 23 whereby the foam is produced and exits the foam production device via tube 26 or 27 according to the position of 3-way valve 25. The foam experiences a pressure of about 414 kPa before it exits the foam production device. When it is released from the foam production device to the environment of atmospheric pressure, it expels excess air which manifests itself as pockets of air within the foam. The formation of a mist is not observed in any of the examples.

The in-line filters used for preparing the foams in the examples have a pore size of 90 micrometers, but generally in-line filters with pore sizes of from 0.5 to 90 micrometers, more preferably from 15 to 90 micrometers are useful for simple foams. For foams containing solids or emulsions, the in-line filters are preferably replaced with strainer elements whose only function is to keep the glass beads in tube 23. Such strainer elements preferably have a nominal pore size of about 440 micrometers. The in-line filters 22 and 24 are connected via a tube 23. The stainless steel tube 23 in the foam production device used in the examples is approximately 25 cm. long by 12.8 cm. external diameter, and is packed with glass beads of 3 mm diameter. Other packed-tube foam generators are described in detail in "A mechanical foam-generator for use in laboratories", by J. F. Fry and R. J. French, J. Appl. Chem., 1, 425–429 (1951). The operation of the foam generating device is known to the skilled artisan.

The properties of the foams produced according to Example 1 are listed in Table 1 below.

In the following tables, "Foam Density[5]" should be regarded as "Apparent Foam Density" due to the fact that foams are weighed in air.

TABLE 1

| air flow (l/min.) | liquid flow[3] (l/min.) | $FQ_T$[1] (%) | Foam density[2] (g/ml) | Liquid volume[4] (ml) | Foam volume[4] (ml) | foam weight[4] (g) | Foam density[5] (g/ml) | FQ[5] |
|---|---|---|---|---|---|---|---|---|
| 5.00 | 0.01 | 99.8 | 0.002 | 35 | 280 | 30.0 | 0.11 | 88 |
| 5.00 | 0.05 | 99.0 | 0.010 | 30 | 280 | 19.5 | 0.07 | 89 |
| 5.00 | 0.10 | 98.0 | 0.019 | 25 | 280 | 16.3 | 0.06 | 91 |
| 4.00 | 0.01 | 99.8 | 0.002 | 30 | 280 | 24.5 | 0.09 | 89 |
| 4.00 | 0.05 | 98.8 | 0.012 | 20 | 280 | 16.0 | 0.06 | 93 |
| 4.00 | 0.10 | 97.6 | 0.024 | 18 | 280 | 13.2 | 0.05 | 94 |
| 3.00 | 0.01 | 99.7 | 0.003 | 25 | 280 | 19.9 | 0.07 | 91 |
| 3.00 | 0.05 | 98.4 | 0.016 | 25 | 280 | 15.5 | 0.06 | 91 |
| 3.00 | 0.10 | 96.8 | 0.032 | 20 | 280 | 13.0 | 0.05 | 93 |
| 2.00 | 0.01 | 99.5 | 0.005 | 20 | 280 | 17.1 | 0.06 | 93 |
| 2.00 | 0.05 | 97.6 | 0.024 | 15 | 280 | 11.1 | 0.04 | 95 |
| 2.00 | 0.10 | 95.2 | 0.048 | 20 | 280 | 14.3 | 0.05 | 93 |

[1]Theoretical foam quality, calculated based on air flow and liquid flow
[2]Theoretical density, calculated according to formula
Foam Density$_T$ = [liquid density × (liquid flow rate/air flow rate)]
[3]density of liquid: 0.96 g/ml
[4]measured values
[5]calculated, based on measured values The properties of the foams produced according to Example 2 are listed in Table 2 below.

TABLE 2

| air flow (l/min.) | liquid flow[3] (l/min.) | $FQ_T$[1] (%) | Foam density[2] (g/ml) | Liquid volume[4] (ml) | Foam volume[4] (ml) | foam weight[4] (g) | Foam density[5] (g/ml) | FQ[5] |
|---|---|---|---|---|---|---|---|---|
| 5.00 | 0.01 | 99.8 | 0.002 | 25 | 280 | 30.0 | 0.11 | 91 |
| 5.00 | 0.05 | 99.0 | 0.010 | 20 | 280 | 19.5 | 0.07 | 93 |
| 5.00 | 0.10 | 98.0 | 0.019 | 20 | 280 | 16.3 | 0.06 | 93 |
| 2.00 | 0.01 | 99.5 | 0.005 | 20 | 280 | 24.5 | 0.09 | 93 |

TABLE 2-continued

| air flow (l/min.) | liquid flow[3] (l/min.) | $FQ_T$[1] (%) | Foam density[2] (g/ml) | Liquid volume[4] (ml) | Foam volume[4] (ml) | foam weight[4] (g) | Foam density[5] (g/ml) | FQ[5] |
|---|---|---|---|---|---|---|---|---|
| 2.00 | 0.05 | 97.6 | 0.024 | 20 | 280 | 16.0 | 0.06 | 93 |
| 2.00 | 0.10 | 95.2 | 0.048 | 20 | 280 | 13.2 | 0.05 | 93 |

[1]Theoretical foam quality, calculated based on air flow and liquid flow
[2]Theoretical density, calculated according to formula
Foam Density$_T$ = [liquid density × (liquid flow rate/air flow rate)]
[3]density of liquid: 0.96 g/ml
[4]measured values
[5]calculated, based on measured values The properties of the foams produced according to Example 3 are listed in Table 1 below.

TABLE 3

| air flow (l/min.) | liquid flow[3] (l/min.) | $FQ_T$[1] (%) | Foam density[2] (g/ml) | Liquid volume[4] (ml) | Foam volume[4] (ml) | foam weight[4] (g) | Foam density[5] (g/ml) | FQ[5] |
|---|---|---|---|---|---|---|---|---|
| 5.00 | 0.01 | 99.8 | 0.002 | 75 | 280 | 70.0 | 0.25 | 73 |
| 5.00 | 0.05 | 99.0 | 0.010 | 85 | 280 | 69.2 | 0.25 | 70 |
| 5.00 | 0.10 | 98.0 | 0.020 | 75 | 280 | 66.3 | 0.24 | 73 |
| 4.00 | 0.01 | 99.8 | 0.002 | 75 | 280 | 70.3 | 0.25 | 73 |
| 4.00 | 0.05 | 98.8 | 0.012 | 75 | 280 | 69.6 | 0.25 | 73 |
| 4.00 | 0.10 | 97.6 | 0.025 | 70 | 280 | 66.4 | 0.24 | 75 |
| 3.00 | 0.01 | 99.7 | 0.003 | 90 | 280 | 71.7 | 0.26 | 68 |
| 3.00 | 0.05 | 98.4 | 0.016 | 90 | 280 | 69.8 | 0.25 | 68 |
| 3.00 | 0.10 | 96.8 | 0.033 | 90 | 280 | 84.9 | 0.30 | 68 |
| 2.00 | 0.01 | 99.5 | 0.005 | 85 | 280 | 74.6 | 0.27 | 70 |
| 2.00 | 0.05 | 97.6 | 0.025 | 80 | 280 | 80.1 | 0.29 | 71 |
| 2.00 | 0.10 | 95.2 | 0.049 | 90 | 280 | 85.9 | 0.31 | 68 |

[1]Theoretical foam quality, calculated based on air flow and liquid flow
[2]Theoretical density, calculated according to formula
Foam Density$_T$ = [liquid density × (liquid flow rate/air flow rate)]
[3]density of liquid: 0.98 g/ml
[4]measured values
[5]calculated, based on measured values

EXAMPLE 4

Examples 1–3 are repeated except that an aqueous solution containing 2 weight percent of the above-described hydroxypropyl methylcellulose, commercially available from The Dow Chemical Company under the Trademark METHOCEL E6PLV is prepared. The solution is colored with a green food dye for increased visibility. Foam is produced as in Examples 1–3. The air flow is 5.0 l/min. The liquid flow is 0.1 l/min. The theoretical foam quality $FQ_T$ is 98.0%. FIG. 2 represents a photograph of the foam flowing through a tube of a foam-generating device. Air-foam boundaries are visible, which indicates that pockets of foam are interspersed with pockets of air. In FIG. 2 the pockets of air flowing through the tube are marked with arrows.

What is claimed is:

1. An aqueous air foam comprising a non-crosslinked cellulose ether selected from the group consisting of $C_1$–$C_3$-alkyl celluloses, $C_1$–$C_3$-alkyl hydroxy-$C_{1-3}$-alkyl celluloses, hydroxy-$C_{1-3}$-alkyl celluloses and mixed hydroxy-$C_1$–$C_3$-alkyl celluloses, the foam having a foam quality FQ of from 60 to 97 percent and the foam quality being defined as FQ (%)=[air volume/(air volume+fluid volume)×100] and comprising no substantial amount of a surfactant other than the cellulose ether.

2. The foam of claim 1 comprising a methyl cellulose or a hydroxypropyl methyl cellulose.

3. The foam of claim 2 wherein the aqueous air foam comprises from 0.01 to 30 weight percent of the cellulose ether, based on the total weight of the cellulose ether and water.

4. The foam of claim 3 having a foam quality FQ of from 65 to 95 percent.

5. The foam of claim 1 wherein the aqueous air foam comprises from 0.01 to 30 weight percent of the cellulose ether, based on the total weight of the cellulose ether and water.

6. The foam of claim 1 comprising no surfactant other than the cellulose ether.

7. The foam of claim 1 having a foam quality FQ of from 65 to 95 percent.

8. A process for agglomerating solid particles wherein an aqueous air foam is contacted with solid particles to be agglomerated, the aqueous air foam comprising a non-crosslinked cellulose ether selected from the group consisting of $C_1$–$C_3$-alkyl celluloses, $C_1$–$C_3$-alkyl hydroxy-$C_{1-3}$-alkyl celluloses, hydroxy-$C_{1-3}$-alkyl celluloses and mixed hydroxy-$C_1$–$C_3$-alkyl celluloses, the foam having a foam quality FQ of from 60 to 97 percent and the foam quality being defined as FQ (%)=[air volume/(air volume+fluid volume)×100] and comprising no substantial amount of a surfactant other than the cellulose ether.

9. The process of claim 8 wherein a powder is agglomerated.

10. The process of claim 8 wherein the foam comprises a methyl cellulose or a hydroxypropyl methyl cellulose.

11. The process of claim 10 wherein the aqueous air foam comprises from 0.01 to 30 weight percent of the cellulose ether, based on the total weight of the cellulose ether and water.

12. The process of claim 11 wherein the foam has a foam quality FQ of from 65 to 95 percent.

13. The process of claim 12 wherein a powder is agglomerated.

14. A process for coating solid particles wherein an aqueous air foam is contacted with the solid particles to be coated, the aqueous air foam comprising a non-crosslinked cellulose ether selected from the group consisting of $C_1$–$C_3$-alkyl celluloses, $C_1$–$C_3$-alkyl hydroxy-$C_{1-3}$-alkyl celluloses, hydroxy-$C_{1-3}$-alkyl celluloses and mixed hydroxy-$C_1$–$C_3$-alkyl celluloses, the foam having a foam quality FQ of from 60 to 97 percent and the foam quality being defined as FQ (%)=[air volume/(air volume+fluid volume)×100] and comprising no substantial amount of a surfactant other than the cellulose ether.

15. The process of claim 14 wherein tablets, granules, pellets, caplets, capsules, lozenges, suppositories, pessaries or implantable dosage forms are coated.

16. The process of claim 14 wherein the foam comprises a methyl cellulose or a hydroxypropyl methyl cellulose.

17. The process of claim 16 wherein the aqueous air foam comprises from 0.01 to 30 weight percent of the cellulose ether, based on the total weight of the cellulose ether and water.

18. The process of claim 17 wherein the foam has a foam quality FQ of from 65 to 95 percent.

19. The process of claim 18 wherein tablets, granules, pellets, caplets, capsules, lozenges, suppositories, pessaries or implantable dosage forms are coated.

* * * * *